(12) United States Patent
Stoll et al.

(10) Patent No.: US 6,344,482 B1
(45) Date of Patent: Feb. 5, 2002

(54) OMEGA-3 FATTY ACIDS IN THE TREATMENT OF BIPOLAR DISORDER

(76) Inventors: Andrew L. Stoll, 35 Old Winter St., Lincoln, MA (US) 01773; Wolfram E. Severus, Badensche Strasse 7, D-10825 Berlin (DE)

( * ) Notice: Subject to any disclaimer, the term of this patent is extended or adjusted under 35 U.S.C. 154(b) by 0 days.

(21) Appl. No.: 09/269,361
(22) PCT Filed: Apr. 23, 1997
(86) PCT No.: PCT/US97/06712
§ 371 Date: Mar. 22, 1999
§ 102(e) Date: Mar. 22, 1999
(87) PCT Pub. No.: WO97/39759
PCT Pub. Date: Oct. 30, 1997

(51) Int. Cl.[7] ............... A61K 31/20; A61K 33/14; A61K 33/00; A61K 31/14
(52) U.S. Cl. ............. 514/560; 424/677; 424/722; 514/642
(58) Field of Search ............ 514/560, 642; 424/677, 722

(56) References Cited

U.S. PATENT DOCUMENTS

| | | | |
|---|---|---|---|
| 4,701,468 A | 10/1987 | Mendy et al. | 514/547 |
| 5,252,333 A | 10/1993 | Horrobin | 424/422 |
| 5,434,183 A | 7/1995 | Larsson-Backström | 514/549 |

FOREIGN PATENT DOCUMENTS

| | | |
|---|---|---|
| EP | 0 289 204 | 11/1988 |
| WO | WO 94/28913 | 12/1994 |

OTHER PUBLICATIONS

Dimmitt SB. "Recent Insights into Dietary Fats and Cardiovascular Disease," *Clin. Exp. Pharmacol. Physiol.* 22: 204–208; 1995.

Sperling RI, et al. "Dietary ω–3 Polyunsaturated Fatty Acids Inhibit Phosphoinositide Formation and Chemotaxis in Neutrophils," *J. Clin. Invest.* 91: 651–660; 1993.

Sperling RI. "Dietary Omega–3 Fatty Acids: Effects on Lipid Mediators of Inflammation and Rheumatoid Arthritis," *Rheumatic Disease Clinics of North America.* 17: 373–389; 1991.

Cohen BM, et al. "Lecithin in Mania: A Preliminary Report," *Am. J. Psychiatry.* 137: 242–243; 1980.

Cohen BM, et al. "Lecithin in the Treatment of Mania: Double–Blind, Placebo–Controlled Trials," *Am. J. Psychiatry.* 139: 1162–1164; 1982.

Schreier Ha. "Mania Responsive to Lecithin in a 13–Year–Old Girl," *Am. J. Psychiatry.* 139: 108–110; 1982.

Stoll Al, et al. "Choline Ingestion Increases the Resonance of Choline–Containing Compounds in Human Brain: An In Vivo Proton Magnetic Resonance Study," *Biol. Psychiatry.* 37: 170–174; 1995.

*Primary Examiner*—William R. A. Jarvis
(74) *Attorney, Agent, or Firm*—Choate, Hall & Stewart

(57) ABSTRACT

The present invention is directed to a method of treating patients with bipolar disorder by administering omega-3 fatty acids.

9 Claims, No Drawings

OMEGA-3 FATTY ACIDS IN THE TREATMENT OF BIPOLAR DISORDER

This application is a 371 of PCT/U.S.97/06712, filed Apr. 23, 1997.

FIELD OF THE INVENTION

The present invention relates to medical treatments for psychiatric disorders. More specifically, it is concerned with novel methods and compositions for treating patients with bipolar disorder.

BACKGROUND OF THE INVENTION

Patients with bipolar disorder suffer recurrent, alternating cycles of mania and depression. In a controlled clinical study performed more than a decade ago, it was reported that lecithin (phosphatidylcholine) has anti-manic properties when administered to such patients (Cohen et al., *Am. J. Psychiatry* 139:1162–1164 (1982); see also Cohen et al., *Am. J. Psychiatry* 137:242–243 (1980); Schreier, *Am. J. Psychiatry* 139:108–110 (1982)). More recent reports have suggested that the beneficial effects observed for lecithin are due primarily to the metabolic release of free choline (Stoll et al., *Biol. Psychiatry* 37:170–174 (1995)).

Although effective in reducing mania, lecithin is not widely used in treating bipolar patients. One of the main reasons for this is that 15–30 grams of lecithin per day must typically be given to a patient in order to obtain a beneficial effect, and the intake of such a large quantity of lipid would, over time, tend to promote cardiovascular disease. An ideal solution to this problem would be to administer a therapeutic agent that has the same beneficial effect as lecithin in controlling mania but which does not have the same adverse effect with respect to cardiovascular disease.

The present invention is directed to phosphatidylcholines in which the $\alpha$ or $\beta$ carbon of glycerol is esterified to an omega-3 fatty acid. These fatty acids are unique among dietary fats in that they inhibit thrombosis and platelet aggregation and can lower blood pressure (see Dimmitt, *Clin. Exp. Pharmacol. Physiol.* 22:204–208 (1995)). Thus, the "omega-3 phosphatidylcholines" disclosed herein produce the same effects as lecithin in bipolar patients due to the release of free choline but reduce, rather than increase, the risk that a patient will suffer a stroke or coronary thrombosis.

In addition, the present invention is directed to a method of treating bipolar disorder using omega-3 fatty acids themselves, i.e. apart from phosphatidylcholine. These may be administered in a purified state, as part of a composition containing other therapeutic agents or as part of another compound, e.g. a triacylglycerol, which is metabolized to release free fatty acid in vivo.

SUMMARY OF THE INVENTION

An evaluation of mood stabilizing agents indicates that all such agents presently used to treat bipolar patients have an inhibitory effect on neuronal signal transduction systems. The present invention is based, in part, upon this discovery and the upon the recognition that omega-3 fatty acids are useful in treating pathological conditions involving excessive cell signal transduction (see e.g., Sperling, *Rheum. Dis. Clinics* 17 (1991); Sperling, et al., *J. Clin. Invest.* 91:651–660 (1993)).

Thus, a method has been developed for treating a human patient for bipolar disorder by administering omega-3 fatty acids at a dosage sufficient to reduce or eliminate the symptoms associated with the disorder, i.e. at a dosage sufficient to reduce the frequency of mood fluctuations or lessen the severity of the mania or depression experienced by such patients. The omega-3 fatty acids should be administered at a dosage of between about 1 and about 30 grams per day. The two most preferred omega-3 fatty acids are eicosapentanoic acid and docosahexanoic acid and these should typically be administered at daily dosages of 2–10 grams and 1–5 grams respectively. The fatty acids may be administered as the sole therapeutic agent or in conjunction with other agents known to be useful in the treatment of bipolar patients. In particular, the fatty acids may be administered with a source either of lithium or choline. In addition, omega-3 fatty acids may be taken by patients as a component of another molecule, e.g. a triacylglycerol, and be metabolically released after ingestion.

The present invention is also directed to an omega-3 phosphatidylcholine useful in the treatment of bipolar disorder, consisting of glycerol esterified at both its $\alpha$ and $\beta$ carbons to fatty acids. At least one, and preferably both, of these fatty acids is an omega-3, fatty acid and the $\gamma$ position of the glycerol must be esterified to phosphocholine. It is preferred that at least one of the esterified fatty acids be either eicosapentanoic acid or docosahexanoic acid. Omega-3 phosphatidylcholines with eicosapentanoic acid esterified to the $\alpha$ carbon and docosahexanoic acid esterified to the $\beta$ carbon and vice versa are the most preferred. In all cases, the $\gamma$ position of the triacylglycerol is esterified to phosphocholine.

In another aspect, the present invention is directed to a pharmaceutical composition comprising one or more of the omega-3 phosphatidylcholines discussed above. The composition should contain sufficient triacylglycerol so that one or more unit doses provides enough agent to reduce or eliminate the symptoms associated with bipolar disorder. In some instances, lithium may be also incorporated into the composition in order to improve therapeutic effects.

The present invention is also directed to a method for treating bipolar disorder in a human patient by administering an omega-3 phosphatidyicholine. It is expected that this phosphatidylcholine will typically be administered at a dosage sufficient to provide between 1 and 30 (preferably between 2 and 8) grams of free omega-3 fatty acid to the patient. Again, administration may be carried out concurrently with the administration of other therapeutic agents such as lithium.

DETAILED DESCRIPTION OF THE INVENTION

In the following description, reference will be made to various methodologies well-known to those skilled in the art of medicine and pharmacology. Such methodologies are described in standard reference works setting forth the general principals of these disciplines. Included among the relevant references are: Goodwin, F. K. and Jamison, K. R., *Manic Depressive Illness*, Oxford University Press (1990); and Bloom, F. and Kupfer, D., *Psychopharmacology. The Fourth Generation of Progress*, Raven Press (1994).

A. Definitions

Bipolar disorder: Bipolar disorder refers to a form of psychosis characterized by adnormally severe mood swings. The patient alternates between episodes of mania and episodes of depression.

Omega-3 fatty acids: Fatty acids are long chain aliphatic molecules beginning with a methyl group and ending with a carboxyl group. Omega-3 fatty acids contain a double bond in the third position from the methyl group. Two common, long chain omega-3 fatty acids are eicosapentanoic acid (20 carbons in length) and docosahexanoic acid (22 carbons in length). These are both found in fish oils Triacylglycerol: Compounds in which the carboxyl groups of fatty acids are esterified to the hydroxyls of all three carbons found in glycerol are referred to as triacylglycerols or triglycerides. Triacylglycerols in which the terminal carbon of glycerol (the "γ carbon") is esterified to phosphocholine are called phosphatidylcholines. The next carbon in the glycerol is referred to herein as the "β carbon," and the following carbon is referred to as the "α carbon."

Omega-3 phosphatidylcholine: As used herein the term "omega-3 phosphatidylcholine" refers to a triacylglycerol in which the γ carbon of glycerol is esterified to phosphocholine, and at least one of the other carbons of glycerol is esterified to an omega-3 fatty acid.

Choline: Choline (hydroxyethyl trimethyl ammonium hydroxide) is considered to be a vitamin of the B complex and is derivable from many foods. Unless otherwise indicated, the term "choline" as used herein, refers not only to the isolated choline molecule (i.e. free choline) but also to any biologically compatible salt of choline (e.g., choline bitartrate).

Lithium: Unless otherwise indicated, the term "lithium" refers to any salt containing lithium as the cationic component.

B. Method of Treating Patients For Bipolar Disorder Using Omega-3 Fatty Acids The present invention is directed to a method for treating human patients for bipolar disorder by administering omega-3 fatty acids. Although the method is not restricted to any one particular type of omega-3 fatty acid, it is preferred that eicosapentanoic acid (EPA) or docosahexanoic acid (DHA) be used. Both EPA and DHA are found in a variety of fish oils and are commercially available in an essentially pure form.

Dosage

The total daily dosage of omega-3 fatty acid administered to a human patient should be at least the amount required to reduce or eliminate the symptoms associated with bipolar disorder. Specifically, the dosage should be high enough to either reduce the severity of the manic and depressive episodes experienced by patients or decrease the frequency at which such episodes occur. Physicians may begin by administering relatively small doses of omega-3 fatty acid (e.g. 1 gram per day) and then adjust the dosage upward as it becomes clear that the patient can tolerate the treatment. The final daily dosage should be between 1 and 30 grams of fatty acid per day, with typical doses ranging between 2 and 10 grams per day. Dosages may be provided in either a single or multiple dosage regiment.

These are simply guidelines since the actual dose must be carefully selected and titrated by the attending physician based upon clinical factors unique to each patient. The optimal daily dose will be determined by methods known in the art and will be influenced by factors such as the age of the patient and other clinically relevant factors. In many cases, a patient will already be taking medications for the treatment of bipolar disorder at the time that treatment with omega-3 fatty acid is initiated. In addition, patients may be taking medications for other diseases or conditions. The other medications may be continued during the time that omega-3 fatty acid is given to the patient, but it is particularly advisable in such cases to begin with low doses to determine if adverse side effects are experienced.

Dosage Forms and Route of Administration

The present invention is not limited to any particular dosage form or route of administration. Oral administration will generally be most convenient; however, the invention is compatible with parenteral, transdermal, sublingual, buccal or implantable routes of administration as well.

Omega-3 fatty acids may be given in a substantially purified form or as part of a pharmaceutical composition containing one or more excipients or flavoring agents. Compositions may also include other active ingredients for the treatment of bipolar disorder, e.g. lithium. Preparations may be solid or liquid and take any of the pharmaceutical forms presently used in human medicine, e.g. tablets, gel capsules, granules, suppositories, transdermal compositions or injectable preparations.

The active ingredient or ingredients may be incorporated into dosage forms in conjunction with any of the vehicles which are commonly employed in pharmaceutical preparations, e.g. talc, gum arabic, lactose, starch, magnesium searate, cocoa butter, aqueous or non-aqueous solvents, oils, paraffin derivatives or glycols. Emulsions such as those described in U.S. PAT. No. 5,434,183, may also be used in which vegetable oil (e.g., soybean oil or safflower oil), emulsifying agent (e.g., egg yolk phospholipid) and water are combined with glycerol. Fatty acids may be incorporated into preparations either in the form of the free acid or as a pharmaceutically acceptable salt. Methods for preparing appropriate formulations are well known in the art (see e.g., *Remington's Pharmaceutical Sciences*, 16th Ed., A. Oslo Ed., Easton, Pa. (1980)).

Manner of Treatment

In order to determine the effect of administered omega-3 fatty acid on mood alteration, patients should be evaluated on a regular basis over an extended period of time, e.g. 1 to 4 weeks. One good manner of carrying out evaluations is for patients to keep a daily diary in which they chart their moods. For example, patients may keep a daily record in which they rate their best and worst moods as either normal, mildly, moderately or severely depressed; and mildly, moderately, or severely manic. These records should help the patient and their physician determine if moods fluctuate less frequently or become less extreme in intensity. Ideally, such a diary should be kept both before and after the administration of omega-3 fatty acid is begun. The evaluation of mood alterations by the patient should also be supplemented with periodic clinical evaluations carried out by a physician.

In some cases, the evaluation discussed above may indicate that mood fluctuations have become so stabilized in a patient as the result of administering omega-3 fatty acid at the initial concentration that no further adjustment in dosage is necessary. In other cases, the dosage of omega-3 fatty acid may be increased in order to obtain a more efficacious result. In general, dosage should not be increased beyond the point at which further stabilization of mood alteration is observed. If adverse side effects are experienced by patients, then dosages may be adjusted in a downward direction accordingly.

The process of adjusting dosage in an upward or downward direction and evaluating the effect of the adjustment on mood changes should be continued until an optimum dosage is discovered, i.e. the dosage at which the patient experiences the best balance between therapeutic effectiveness and discomfort due to side effects. In cases where adverse side effects are not experienced, the optimal dosage is the lowest dose resulting in maximum stabilization of mood fluctuation.

Omega-3 fatty acids may be used in combination with other agents effective at treating bipolar disorder, e.g. lithium or choline. These other agents may either be given together with omega-3 fatty acid in a single dosage form, or they may be administered separately. Choline should be administered at an initial dose of about 50 mg of free choline per kg of body weight, supplied either as a single unit dose or, preferably, divided into multiple doses during the day. The choline may be administered either as a free base or in the form of a pharmaceutically acceptable salt. The final dosage of choline should typically be between about 2 and about 8 grams of free choline per day.

Patients taking lithium should continue taking the drug during the time at which choline and/or omega-3 fatty acid treatment is begun. Optimal dosages for each of the drugs may then be determined sequentially. For example, choline administration may be initiated and then optimized followed by the initiation and optimization of omega-3 fatty acid treatment. The problem of adjusting the dosages of multiple therapeutic agents is one that is routinely encountered by physicians and can be solved using well-established procedures similar to those discussed herein.

Kits

Individual preparations containing omega-3 fatty acid and other therapeutic agents for bipolar disorder, such as choline or lithium, may be provided in the form of a kit, comprising a carrier (e.g. a box or bag) compartmentalized to receive one or more components (bottles, vials, packets, etc.) in close confinement. Such a kit will be carried by patients with bipolar disorder and will typically contain written instructions concerning the way in which the enclosed drugs should be taken, potential side effects, etc. The kit should be portable, and be generally convenient for use by patients.

C. Omega-3 Phosphatidylcholines

The present invention is also directed to omega-3 phosphatidylcholines in which glycerol is esterified at its γ carbon to phosphocholine and at least one of the fatty acids esterified to either the α or β carbons is an omega-3 fatty acid. It is preferred that both the α carbon and β carbon of glycerol be esterified to an omega-3 fatty acid, with the preferred fatty acids being EPA and DHA. The most preferred phosphatidylcholines contain both DHA and EPA, one esterified at the α carbon of glycerol and the other at the β carbon.

The phosphatidylcholines of the present invention may be synthesized using standard techniques well known in the art, see e.g. U.S. Pat. No. 4,701,468. One suitable method is to synthesize the "omega-3 phosphatidylcholines" from commercially available precursor lyso-phosphatidylcholines. Specifically, a lyso-phos-phatidylcholine is acylated by combining the desired omega-3 fatty acid anhydride (e.g. from EPA or DHA) and 4-pyrrolidinopyridine as a catalyst (1.2 equivalents) in alcohol-free chloroform. Depending on the reaction conditions and the relative proportions of fatty acid, several different omega-3 phosphatidylcholine species will be generated. Using EPA and DHA, four major species will occur: dieicosapent-anoylphosphatidylcholine, didocosahexanoylphosphatidylcholine, 1-eicosapentanoyl, 2-docosahexanoylphosphatidylcholine, and 1-docosahexanoyl, 2-eicosapentanoylphosphatidylcholine. The specific phosphatidylcholines of interest may then be isolated by well-established chromatographic methods.

D. Method of Treating Bipolar Disorder Using Omega-3 Phosphatidylcholines

The omega-3 phosphatidylcholines described above may be used for treating humans with bipolar disorder in the same manner and following the same procedures as those discussed in connection with omega-3 fatty acids. The phosphatidylcholines may be given in a substantially purified form or as part of a pharmaceutical composition, It is expected that optimized dosages will have sufficient omega-3 phosphatidylcholine to deliver between about one and about 30 grams of free omega-3 fatty acid per day, with the preferred daily dose being between 1 and 10 grams. Patients should keep diaries of daily mood fluctuations and be evaluated by a physician on a regular basis to determine the effect of treatment. Based upon such evaluations, dosages may be increased or decreased as needed.

As with omega-3 fatty acids, the omega-3 phosphatidylcholines may be delivered by any route and are compatible with any dosage form. Oral dosage forms such as tablets, capsules, powder packets and liquid solutions will generally be preferred. Therapeutically inert agents may be added to improve the palatability of preparations, and additional therapeutic agents may be included. It will be appreciated that one particularly attractive composition would include both a source of lithium as well as omega-3 phosphatidylcholine.

In cases where parenteral administration is elected as the route of administration, preparations containing omega-3 phosphatidylcholine. may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

Omega-3 phosphatidylcholine and other agents useful in treating bipolar patients, preferably lithium or choline may be provided as separate components in the form of a kit designed to be carried and used by bipolar patients. The kit would contain written instructions concerning the way in which the enclosed agents should be taken and other pertinent information.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method of treating a human patient for bipolar disorder, comprising administering an omega-3 fatty acid to said patient at a dosage sufficient to reduce or eliminate the symptoms of said disorder, wherein said symptoms are symptoms of mania and symptoms of depression.

2. The method of claim 1, wherein said omega-3 fatty acid is administered at a dose of between about 1 and about 30 grams per day.

3. The method of claim 1, wherein said omega-3 fatty acid is in a substantially pure form.

4. The method of claim 1, wherein said omega-3 fatty acid is eicosapentanoic acid.

5. The method of claim 4, wherein said eicosapentanoic acid is administered at a dose of between about 2 and about 10 grams per day.

6. The method of claim 1, wherein said omega-3 fatty acid is docosahexanoic acid.

7. The method of claim 6, wherein said docosahexanoic acid is administered at a dose of between about 1 and about 5 grams per day.

8. The method of claim 1, further comprising administering a source of lithium to said patient at a dose sufficient to reduce or eliminate the symptoms of said disorder.

9. The method of claim 1, further comprising administering a source of choline to said patient at a dose effective at reducing or eliminating the symptoms of said disorder.

* * * * *